United States Patent
Scott et al.

(10) Patent No.: US 7,267,546 B2
(45) Date of Patent: Sep. 11, 2007

(54) LIGHT METER FOR DETECTING AND MEASURING INTENSITY OF TWO OR MORE WAVELENGTHS OF LIGHT

(75) Inventors: Robert R. Scott, Riverton, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 428 days.

(21) Appl. No.: 10/914,479

(22) Filed: Aug. 9, 2004

(65) Prior Publication Data

US 2006/0028639 A1    Feb. 9, 2006

(51) Int. Cl.
*G61C 3/00*   (2006.01)
*G01J 1/42*   (2006.01)

(52) U.S. Cl. .................. 433/29; 433/27; 433/709; 356/218

(58) Field of Classification Search ........ 356/213–228, 356/39–41, 407; 250/252.1; 433/26, 29; 600/179, 160
See application file for complete search history.

(56) References Cited

U.S. PATENT DOCUMENTS

| | | | |
|---|---|---|---|
| 4,878,072 A | 10/1989 | Reinten | 347/236 |
| 5,382,799 A | 1/1995 | May | 250/372 |
| 5,418,369 A | 5/1995 | Moore et al. | 250/372 |
| 5,424,547 A | 6/1995 | Stark et al. | 250/372 |
| 5,486,914 A * | 1/1996 | Denove et al. | 356/221 |
| 5,497,004 A | 3/1996 | Rudolph et al. | 250/372 |
| 5,822,053 A | 10/1998 | Thrailkill | 356/237.1 |
| 5,872,623 A | 2/1999 | Stabile et al. | 356/73 |
| 5,902,105 A * | 5/1999 | Uejima et al. | 433/27 |
| 5,908,294 A * | 6/1999 | Schick et al. | 433/29 |
| 6,023,066 A | 2/2000 | Cain et al. | 250/372 |
| 6,133,994 A * | 10/2000 | Mathews et al. | 356/41 |
| 6,144,036 A | 11/2000 | Danilychev | 250/372 |
| 6,201,250 B1 | 3/2001 | Morlock | 250/372 |
| 6,276,933 B1 * | 8/2001 | Melnyk et al. | 433/26 |
| 6,278,120 B1 | 8/2001 | May | 250/372 |
| 6,426,503 B1 | 7/2002 | Wuest | 250/372 |
| 6,459,087 B1 | 10/2002 | Kaas | 250/372 |
| 6,486,945 B1 | 11/2002 | Haerle et al. | 356/218 |
| 6,525,819 B1 * | 2/2003 | Delawter et al. | 356/406 |
| 6,551,493 B2 | 4/2003 | Mori et al. | 205/775 |
| 6,566,656 B2 | 5/2003 | May et al. | 250/372 |
| 6,692,252 B2 * | 2/2004 | Scott | 433/29 |

(Continued)

OTHER PUBLICATIONS

A Powerful Revolution in LED Technology (Mar. 2004) http://www.denmat.com/solsheet/allegro/allegro_info.htm.

(Continued)

Primary Examiner—Sang H. Nguyen
(74) Attorney, Agent, or Firm—Workman Nydegger

(57) ABSTRACT

A light meter for detecting two or more different wavelengths of light and methods for determining whether a light source configured to emit light at two or more dominant wavelengths is working properly. The inventive light meter includes a housing, two or more receiving means for receiving light energy emitted by an external light source wherein each receiving means is configured to receive light energy of a desired wavelength, detecting means for detecting and measuring light energy received by the receiving means, and display means for providing a visual indication of the existence and intensity of one or more wavelengths of light energy received by the receiving means.

17 Claims, 3 Drawing Sheets

U.S. PATENT DOCUMENTS

| | | |
|---|---|---|
| 6,719,558 B2* | 4/2004 | Cao .......................... 433/29 |
| 6,940,659 B2* | 9/2005 | McLean et al. ............. 359/709 |
| 2002/0024653 A1 | 2/2002 | Jung et al. ................... 356/73 |
| 2002/0121608 A1 | 9/2002 | Sandstrom et al. ......... 250/372 |
| 2003/0030808 A1 | 2/2003 | Marshall et al. ............ 356/406 |
| 2003/0081207 A1 | 5/2003 | Wechsler et al. ........... 356/318 |
| 2003/0150998 A1 | 8/2003 | Shin et al. .................. 250/372 |
| 2003/0178571 A1 | 9/2003 | Nayfeh et al. .............. 250/372 |
| 2003/0230725 A1 | 12/2003 | Wong ......................... 250/372 |
| 2003/0234365 A1 | 12/2003 | Wipenmyr .................. 250/372 |
| 2004/0021087 A1 | 2/2004 | Tokhtuev et al. ........... 250/372 |
| 2004/0101802 A1* | 5/2004 | Scott ........................... 433/29 |

OTHER PUBLICATIONS

"3M ESPE Introduces New LED Curing Light"(Mar. 2004) http://cms.3m.com/cms/US/en/2-21/iFzkeFZ/view.jhtml.

"Archer & White Handpiece Supercenter 2003"(Mar. 2004) http://www.archerwhite.com/p36.html.

Winter 2004 Specials!, "The Number One Choice - LED Curing Lights With Portability, Thermally Cool Light Output, And Long-Lasting Diodes".

* cited by examiner

LIGHT METER FOR DETECTING AND MEASURING INTENSITY OF TWO OR MORE WAVELENGTHS OF LIGHT

BACKGROUND OF THE INVENTION

1. The Field of the Invention

The invention relates to a device and related method for detecting and measuring light output of an external light source (e.g., an LED dental curing light).

2. The Relevant Technology

In the field of dentistry, dental cavities are often filled and/or sealed with photosensitive compounds that are cured by exposure to radiant energy, such as visible light. These compounds, commonly referred to as light-curable compounds, are placed within dental cavity preparations or onto dental surfaces where they are subsequently irradiated by light. The radiated light causes photosensitive components within the compounds to polymerize, thereby hardening the light-curable compounds within the dental cavity preparation or another desired location.

Existing light-curing devices are typically configured with a light source, such as a quartz-tungsten-halogen (QTH) lamp bulb or an LED light source. QTH bulbs are particularly useful because they are configured to generate a broad spectrum of light that can be used to cure a broad range of products. In particular, a QTH bulb is typically configured to emit a continuous spectrum of light in a preferred range of about 350 nm to about 500 nm. Some QTH bulbs may even emit a broader spectrum of light, although filters are typically used to limit the range of emitted light to the preferred range mentioned above.

A broad light spectrum (e.g., that emitted by a QTH bulb) can be beneficial in that it allows curing of multiple types of materials. For example, camphorquinone is a common photo-initiator that is most responsive to blue light having a wavelength of about 455 nm to about 470 nm. Other light-curable products, however, including many adhesives are cured when they are irradiated by light wavelengths in the 350 nm to 400 nm range. Accordingly, QTH bulbs can be used to cure both camphorquinone initiated products as well as other adhesives.

Another problem with existing light-generating devices is that they are not very efficient. In particular, large quantities of radiation energy is lost due to filtering, dissipation, and light that is not properly directed into the patient's mouth. This is a problem because it generally results in increased power requirements for generating a desired output of radiation.

In an attempt to overcome problems of low efficiency and excess heat generation of QTH and other bulb light sources, some light-generating devices have been manufactured using alternative light generating sources, such as light-emitting diodes (LEDs) which are generally configured to only radiate light at specific wavelengths, thereby eliminating the need for special filters and generally reducing the amount of input power required to generate a desired output of radiation.

LEDs are particularly suitable light sources because they generate much less heat than QTH bulbs, thereby enabling the LEDs to be placed at the tip of the curing lights and to be inserted directly within the patient's mouth. This is particularly useful for reducing or eliminating the need for light guides such as optical fiber wands.

One limitation of LEDs, however, is that they are only configured to emit a narrow spectrum of light. For example, a 455 nm LED or LED array will generally only emit light having a spectrum of 455 nm±30 nm. Accordingly, a 455 nm LED light source will be well designed to cure camphorquinone initiated products, but will not be suitable for curing adhesives that are responsive to light in the 380 nm±30 nm range. Likewise, a 380 nm LED light source may be suitable to cure some adhesives, but will be unsuitable for curing camphorquinone initiated products. As a result, LED curing lights including a plurality of different LEDs have been developed to allow a single LED curing light to be used to cure both camphorquinone initiated products as well as other adhesives.

Because bulbs emit a wide spectrum, they are able to emit both visible and UV wavelengths simultaneously. This makes determining when a bulb has burned out simple, because it can be determined by a quick visual inspection. This is not the case with LED curing lights including a plurality of different LEDs (e.g., blue and UV). Because each LED emits a narrow spectrum of light, it takes two or more LEDs to emit both visible (e.g., blue) and UV wavelengths simultaneously. The condition of an LED emitting visible wavelengths of light (e.g., blue) is easily ascertained, but it can be very difficult to determine the condition of an LED that emits UV wavelengths of light. This makes it difficult to determine when a UV LED has burned out, as it cannot be determined by visual inspection.

In view of the foregoing, there exists a need for a device and method for determining the existence and intensity of light output by an LED curing light, particularly one including UV LEDs.

BRIEF SUMMARY OF THE INVENTION

The present invention is directed to a light meter for detecting two or more different wavelengths of light. The inventive light meter includes a housing, two or more receiving means for receiving light energy emitted by an external light source wherein each receiving means is configured to receive light energy of a desired wavelength, detecting means within the housing for detecting and measuring light energy received by the receiving means, and display means for providing a visual indication of the existence and intensity of one or more wavelengths of light energy received by the receiving means.

According to one embodiment, the two or more receiving means may comprise two or more LEDs or LED arrays capable of emitting light at different wavelengths. LEDs and LED arrays exhibit a push-pull characteristic. When a voltage is applied to an LED, it emits light of a particular wavelength having an intensity proportional to the magnitude of the voltage. When light of that wavelength is directed towards the LED, it generates a voltage proportional to the intensity of the light. Because of this characteristic, LEDs and LED arrays can be used as receiving means.

For example, according to one embodiment, at least one of the two or more LEDs or LED arrays is capable of emitting UV light (e.g., 380 nm as the dominant mean wavelength). According to another embodiment, at least one of the two or more LEDs or LED arrays is capable of emitting blue light (e.g., 455 nm as the dominant mean wavelength). The light meter may include additional LEDs or LED arrays capable of emitting various other wavelengths of light, as desired. The light meter may further include an additional sensor (e.g., a silicon sensor) for detecting overall broadband light output of the external light source being metered.

According to one embodiment, the detecting means may comprise circuitry for measuring any electrical potential generated by the two or more LEDs, LED arrays, or other receiving means when irradiated with light energy.

According to one embodiment, the display means may comprise an LED bar display, an analog needle display, or a digital character display for providing a visual indication of the existence and intensity of one or more wavelengths of light energy received by the two or more receiving means (e.g., LEDs or LED arrays).

The light meter may also include means for communicating with a secondary device. Such means for communicating may comprise a transmitter (e.g., an infrared or radio frequency transmitter), a receiver, an input jack, or an output jack for connecting and/or communicating with a, secondary device (e.g., a personal digital assistant, a computer, calibration equipment, or another device).

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

I. Introduction

A detailed description of the invention will now be provided with specific reference to Figures illustrating preferred embodiments of the invention. It will be appreciated that like structures will be provided with like reference designations. To provide context for interpreting the scope of the invention, certain terms used throughout the application will now be defined.

The term "LED," as used herein, generally refers to one or more light emitting diodes (LEDs), one or more LED arrays, or any combination of the above. The light emitted by an individual LED includes a limited spectrum of wavelengths, the peak of which corresponds with the rating of the LED.

Figure 1:
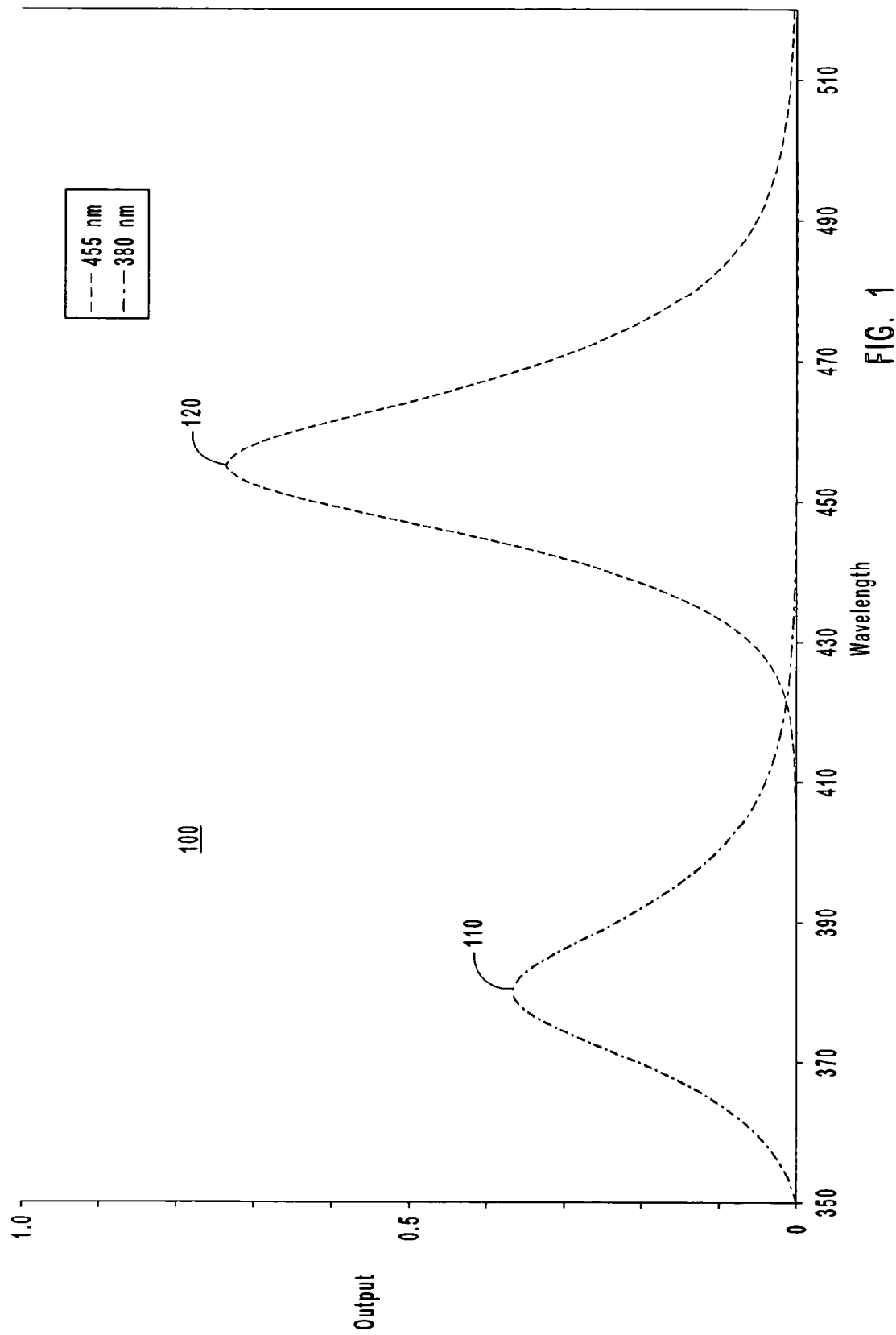
FIG. 1 illustrates the intensity of light output by an exemplary 380 nm UV LED and a 455 nm blue LED as a function of wavelength.

FIG. 1 illustrates a graph 100 that charts the spectral output emitted by a 380 nm LED light source and a 455 nm LED light source. The values given in the y-axis are generic such that no specific representation as to the actual power output should be assumed.

The 380 nm LED spectrum 110 ranges from about 340 nm to about 430 nm, with the most intense output of light being within the range of about 360 nm to about 400 nm. The 455 nm LED spectrum 120 ranges from about 405 nm to about 505 nm, with the most intense output of light being within the range of about 425 nm to about 475 nm.

II. Exemplary Light Meter

Figure 2:
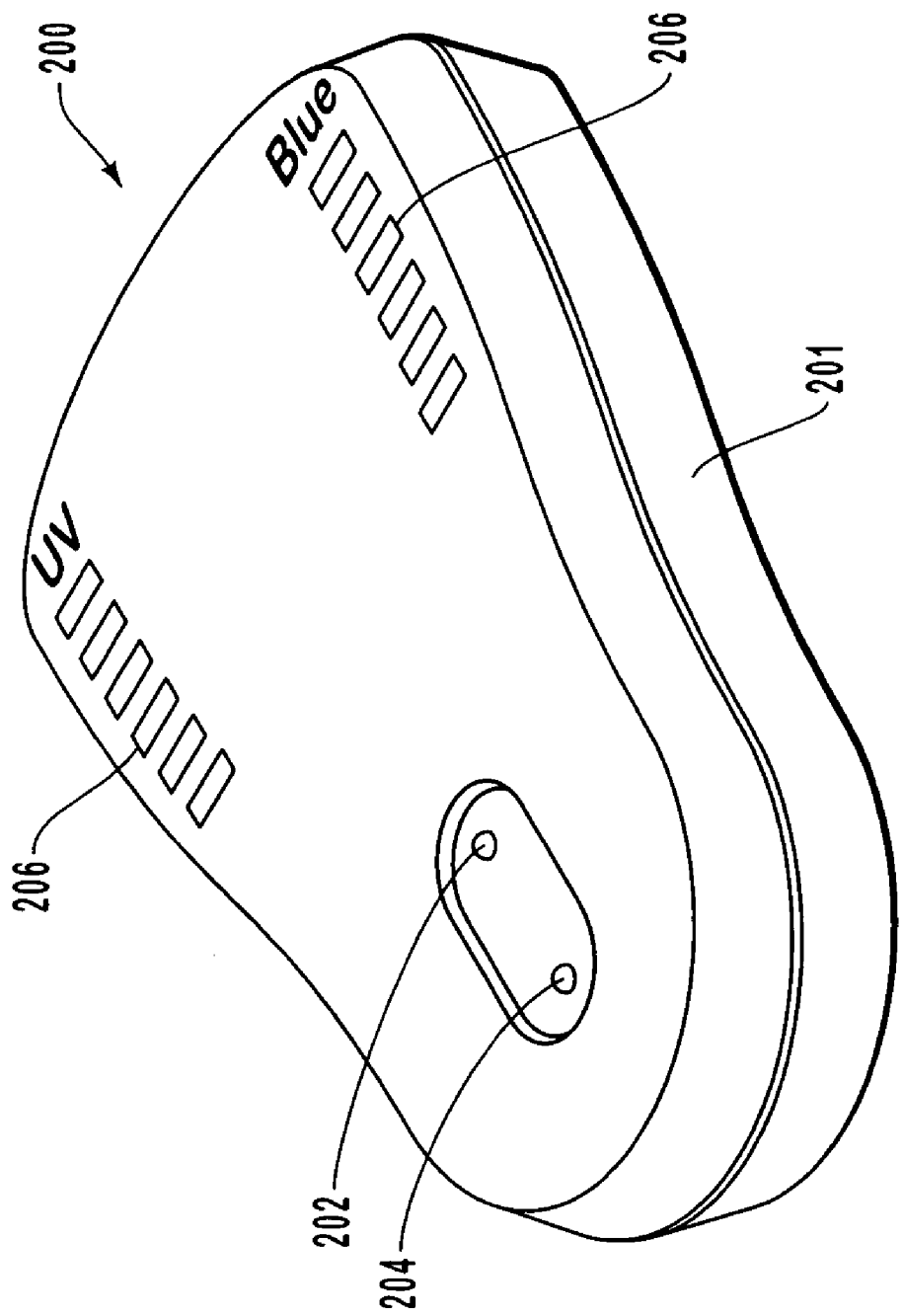
FIG. 2 is a perspective view of an exemplary light meter.

FIG. 2 illustrates an exemplary light meter 200, which includes a housing 201, two LEDs 202 and 204 capable of emitting light at different wavelengths, circuitry (not shown) for measuring any electrical potential generated by the LEDs as they receive light of their associated wavelengths, and a display 206 for providing a visual indication of the existence and intensity of light energy received by the LEDs 202 and 204.

LEDs 202 and 204 are examples of receiving means for receiving light energy emitted by an external light source. The LEDs are selected so as to be capable of emitting a desired wavelength. Because of the push-pull characteristic of LEDs, the wavelength rating of the LED corresponds to the wavelength of light which the LED is configured to receive. According to one embodiment, the LEDs may include an LED capable of emitting blue light (e.g., having a mean dominant wavelength of about 455 nm) and an LED capable of emitting UV light (e.g., having a mean dominant wavelength of about 380 nm). Such an embodiment is useful in testing dental curing lights including blue and/or UV LEDs. Although the light meter 200 includes two LEDs 202 and 204, it is to be understood that additional LEDs of any desired wavelength and arrangement may be included.

LED bar display 206 is an example of display means for providing a visual indication of the existence and intensity of one or more wavelengths of light energy received by the receiving means (e.g., LEDs 202 and 204). In the illustrated embodiment, LED bar display 206 comprises a plurality of LEDs configured in two bar columns, although other LED configurations could be used. The LED bars light up to indicate the existence and intensity of a particular wavelength of light (e.g., blue or TV). For example, the left bar column may be used for displaying information about UV wavelengths, while the right bar column may be used for displaying information about blue wavelengths. The LED bar display may include LEDs of different colors (e.g., red on the bottom, yellow in the middle, and green on top) to indicate output intensity. Alternatively, the display may comprise an analog needle display, a digital character display (e.g., LCD or LED), or any other suitable visual display.

According to one embodiment, the light meter 200 may also include a silicon sensor (not shown) for detecting the overall broadband light output emitted by an external light source.

According to another embodiment, the light meter 200 may also include means (not shown) for communicating with a secondary device (e.g., a personal digital assistant, a computer, calibration equipment, or another device). Means for communicating may comprise one or more of a transmitter (e.g., an infrared or radio frequency transmitter), a receiver, an input jack, or an output jack.

III. Exemplary Method of Use

Figure 3:
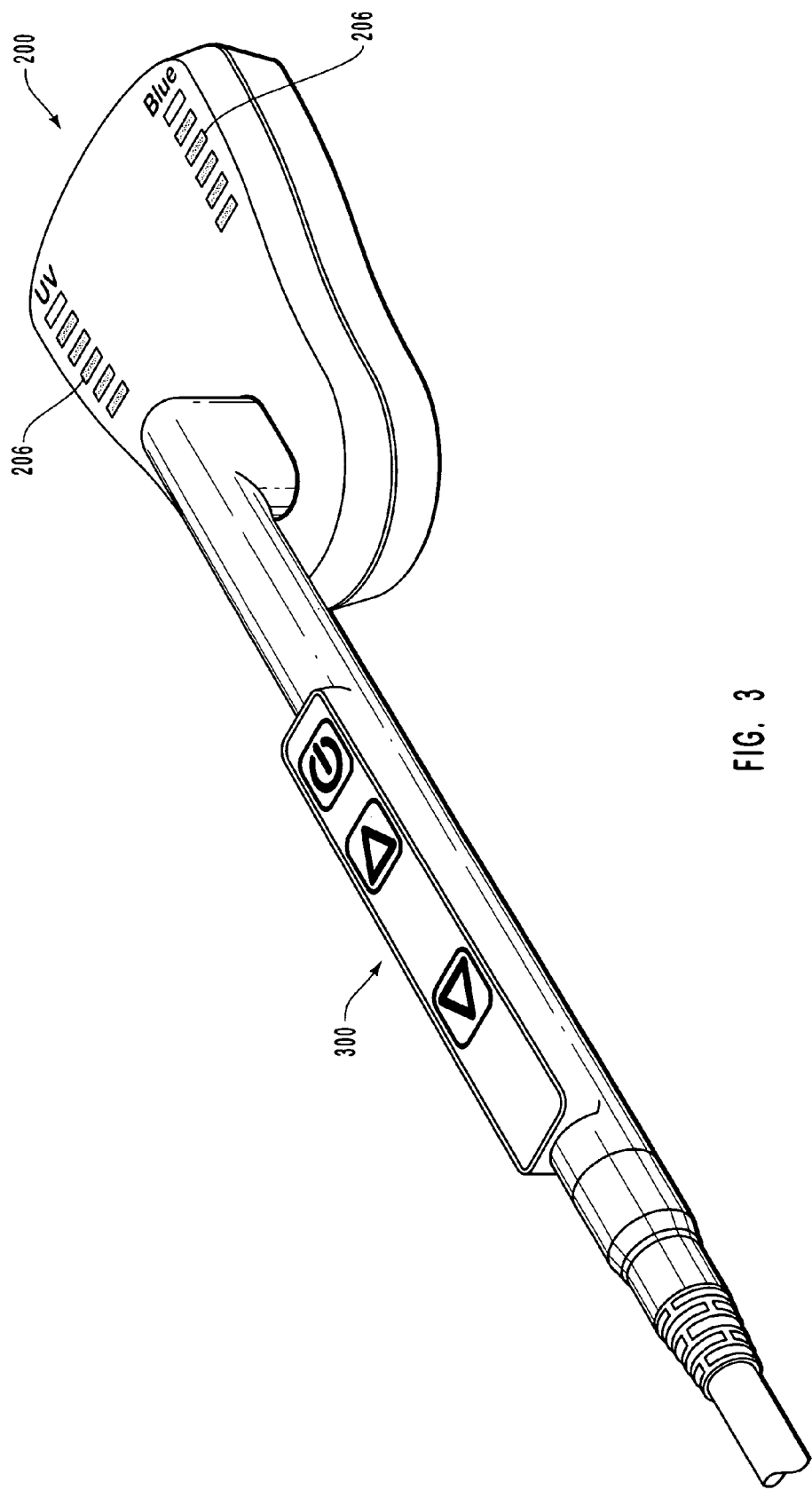
FIG. 3 is a perspective view of the light meter of FIG. 2 being used to detect the existence and intensity of specific wavelengths of light emitted by a dental curing light.

FIG. 3 illustrates the light meter 200 being used to measure the output of a dental curing light 300, although the light meter 200 could be used to measure light output of any desired external light source. The dental curing light 300 is positioned so as to direct emitted light energy towards the two or more receiving means for receiving light (e.g., two or more LEDs 202 and 204). The external light source (e.g., the dental curing light 300) is activated so as to emit light energy, and the user is able to read the display means (e.g., LED a bar display 206) so as to determine the existence and intensity of particular wavelengths of light energy emitted by the external light source 300.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. In a dental light curing system wherein a dental curing light is provided with a light output end having at least two LEDs of differing wavelengths that are adapted for use in curing polymerizable dental compositions responsive to the different wavelengths, a light meter for detecting when one or both LEDs of the dental curing light are outputting insufficient light to perform desired polymerization of the polymerizable materials, the light meter comprising:
 a housing having a receptacle for receiving therein the light output end of the dental curing light, and in which there are mounted first and second receiving means for responding to received light energy emitted by an external light source by outputting a corresponding light intensity to that received,
  said first receiving means responding only to the wavelength output by one of the two LEDs of the dental curing light, and
  said second receiving means responding only to the wavelength output by the other LED of the dental curing light;
 said housing further having first and second display means visibly mounted on an upper surface thereof,
  said first display means outputting a visual indication of the light intensity of only one of the LEDs of the dental curing light,
  said second display means outputting a visual indication of the light intensity of only the other of the LEDs of the dental curing light, and
  wherein said first and second display means simultaneously provide respective visual indications so that the first and second display means provide simultaneous detection of when one or both LEDs of the dental curing light are outputting insufficient light to perform desired polymerization of the polymerizable materials.

2. A light meter as recited in claim 1, wherein said two or more receiving means comprise two or more LEDs or LED arrays capable of emitting light at different dominant wavelengths.

3. A light meter as recited in claim 2, further comprising circuitry for measuring any electrical potential generated by the two or more LEDs or LED arrays when irradiated with light energy.

4. A light meter as recited in claim 2, wherein said display means comprises one of an LED bar display, an analog needle display, or a digital character display for providing a visual indication of the existence and intensity of two or more wavelengths of light energy received by the two or more LEDs or LED arrays.

5. A light meter as recited in claim 1, further comprising means for communicating with a secondary device.

6. A light meter as recited in claim 5, wherein said means for communicating with a secondary device comprises at least one a transmitter, a receiver, an input jack, or an output jack.

7. In a dental light curing system wherein a dental curing light is provided with a light output end having at least two LEDs of differing wavelengths that are adapted for use in curing polymerizable dental compositions responsive to the different wavelengths, a light meter for detecting when one or both LEDs of the dental curing light are outputting insufficient light to perform desired polymerization of the polymerizable materials, the light meter comprising:
 a housing having a receptacle for receiving therein the light output end of the dental curing light, and in which there are mounted first and second receiving LEDs that are adapted to respond to received light energy emitted by an external light source by outputting a corresponding light intensity to that received,
  said first receiving LED adapted to respond only to the wavelength output by one of the two LEDs of the dental curing light, and
  said second receiving LED adapted to respond only to the wavelength output by the other LED of the dental curing light;
 circuitry that measures any electric potential generated by the first and second receiving LEDs when irradiated with light energy within the receptacle of said housing; and
 said housing further having first and second displays mounted on an upper surface thereof,
  said first display outputting a visual indication of the light intensity of only one of the LEDs of the dental curing light,
  said second display outputting a visual indication of the light intensity of only the other of the LEDs of the dental curing light, and
  wherein said first and second displays simultaneously provide respective visual indications so that the first and second displays provide simultaneous detection of when one or both LEDs of the dental curing light are outputting insufficient light to perform desired polymerization of the polymerizable materials.

8. A light meter as recited in claim 7, wherein at least one of the two LEDs is capable of emitting UV light.

9. A light meter as recited in claim 8, wherein said UV light has a mean dominant wavelength of about 380 nm.

10. A light meter as recited in claim 7, wherein at least one of the two LEDs is capable of emitting blue light.

11. A light meter as recited in claim 10, wherein said blue light has a mean dominant wavelength of about 455 nm.

12. A light meter as recited in claim 7, further comprising a silicon sensor for detecting the overall light output emitted by an external light source.

13. A light meter as recited in claim 7, further comprising a transmitter for communicating with a secondary device.

14. A light meter as recited in claim 13, wherein said transmitter comprises one of an infrared or radio frequency transmitter.

15. In a dental light curing system wherein a dental curing light is provided with a light output end having at least two LEDs of differing wavelengths that are adapted for use in curing polymerizable dental compositions responsive to the different wavelengths, and a light meter comprising a housing having a receptacle for receiving therein the light output end of the dental curing light, and in which there are mounted first and second receiving means for responding to received light energy emitted by an external light source by outputting a corresponding light intensity to that received, said first receiving means responding only to the wavelength output by one of the two LEDs of the dental curing light, and said second receiving means responding only to the wavelength output by the other LED of the dental curing light, said housing further having first and second display means visibly mounted on an upper surface thereof, said first display means outputting a visual indication of the light intensity of only one of the LEDs of the dental curing light, said second display means outputting a visual indication of the light intensity of only the other of the LEDs of the dental curing light, a method of detecting when one or both LEDs of the dental curing light are outputting insufficient light to perform desired polymerization of the polymerizable materials comprising:

placing the light output end of the dental curing light in the receptacle of the housing and activating the at least two LEDs of differing wavelengths;

a steps for one of the receiving means responding to the wavelength of one of the LEDs and the other receiving means responding to the wavelength of the other LED of the light output end of the dental curing light; and a step for simultaneously outputting at the first and second display means a visual indication of whether one or both LEDs of the dental curing light are outputting insufficient light to perform desired polymerization of the polymerizable materials.

16. A method as recited in claim 15, wherein the light output end of the dental curing light includes at least one LED or LED array configured to emit light in the blue light spectrum and at least one other LED or LED array configured to emit light in the UV spectrum.

17. A method as recited in claim 15, wherein a steps for one of the receiving means responding to the wavelength of one of the LEDs and the other receiving means responding to the wavelength of the other LED of the light output end of the dental curing light comprises receiving emitted light from a first LED of the dental curing light at a firs LED or LED array configured to emit light in the blue light spectrum and receiving emitted light from a second LED of the dental curing light at a second LED or LED array configured to emit light in the UV spectrum.

* * * * *

UNITED STATES PATENT AND TRADEMARK OFFICE
CERTIFICATE OF CORRECTION

| | |
|---|---|
| PATENT NO. | : 7,267,546 B2 |
| APPLICATION NO. | : 10/914479 |
| DATED | : September 11, 2007 |
| INVENTOR(S) | : Scott et al. |

Page 1 of 1

It is certified that error appears in the above-identified patent and that said Letters Patent is hereby corrected as shown below:

Column 1
Line 43, change "Another" to --A--

Column 3
Line 13, change "a," to --a--

Column 4
Line 40, change "TV" to --UV--

Column 6
Line 3, after "one" remove [a]

Column 7
Line 19 Claim 15, change "a steps" to --a step--

Column 8
Line 11 Claim 16, change "a steps" to --a step--
Line 16 Claim 17, change "firs" to --first--

Signed and Sealed this

Fifth Day of August, 2008

JON W. DUDAS
*Director of the United States Patent and Trademark Office*